United States Patent [19]

Burrows

[11] Patent Number: 5,057,212

[45] Date of Patent: Oct. 15, 1991

[54] WATER CONDUCTIVITY MONITOR AND CIRCUIT WITH EXTENDED OPERATING LIFE

[76] Inventor: Bruce D. Burrows, 25581 Via Paladar, Valencia, Calif. 91355

[21] Appl. No.: 491,310

[22] Filed: Mar. 9, 1990

[51] Int. Cl.$^5$ ............................................. B01D 35/43
[52] U.S. Cl. ....................................... 210/85; 210/94; 210/96.2; 324/439; 324/446; 340/603; 340/657; 340/815.1
[58] Field of Search ................ 73/865.9, 61 R, 866.3; 210/85, 94, 96.1, 96.2, 746; 324/439, 441–444, 415, 446; 340/603, 815.01, 815.1, 657

[56] References Cited

U.S. PATENT DOCUMENTS

| | | | |
|---|---|---|---|
| 3,990,066 | 11/1976 | Malmgren | 210/85 |
| 4,383,221 | 5/1983 | Morey et al. | 324/442 |
| 4,762,611 | 8/1988 | Schipper | 210/96.2 |
| 4,849,098 | 7/1939 | Wilcock et al. | 210/85 |
| 4,851,818 | 7/1989 | Brown et al. | 210/85 |

FOREIGN PATENT DOCUMENTS 63-75650  4/1988  Japan .................................. 324/444

Primary Examiner—Robert A. Dawson
Assistant Examiner—Joseph Drodge
Attorney, Agent, or Firm—Kelly, Bauersfeld & Lowry

[57] ABSTRACT

A water quality monitor is provided for use in a purified water supply system of the type having a reverse osmosis unit or the like for producing relatively purified water from an ordinary tap or feed water supply. The monitor includes a control circuit having eletrodes in contact with the purified and tap water supplies. The control circuit is activated by depression of a test button to produce a short duration pulse of one polarity which is connected to the electrodes for use in determining the water conductivities. The control circuit compares the conductivities of the purified and tap water supplies, wherein this comparison represents the operational efficiency of the purification system in removing contaminants from the incoming tap water. The control circuit responds to this comparison to illuminate an appropriate indicator light or the like and thereby indicate the operational state of the purification system. The control circuit maintains the appropriate indicator light in an illuminated state until the test button is released, at which time the control circuit couples a short duration pulse of opposite polarity to the electrodes for preventing or minimizing electrode corrosion and/or accumulation of ionic deposit thereon. The generation of a short duraction pulse to determine conductivity. In combination with illumination of the appropriate indicator light only until the test button is released, minimizes circuit power consumption and thereby extends monitor service life when a battery power source is used.

17 Claims, 2 Drawing Sheets

WATER CONDUCTIVITY MONITOR AND CIRCUIT WITH EXTENDED OPERATING LIFE

BACKGROUND OF THE INVENTION

This invention relates generally to improvements in water purification systems of the type having a reverse osmosis unit or the like for removing dissolved ionic material and other contaminants from an ordinary supply of tap or feed water. More particularly, this invention relates to a relatively simple and reliable water quality or purity monitor for incorporation into a water purification system, wherein the monitor includes improved means for indicating the operational efficiency of the reverse osmosis unit.

Water purification systems in general are relatively well-known in the art of the type having a reverse osmosis unit for converting an incoming supply of ordinary tap or feed water into relatively purified water for use in cooking, drinking, etc. In general terms, the reverse osmosis unit includes a semi-permeable membrane through which a portion of the feed water supply is passed, such that the membrane acts essentially as a filter to remove dissolved metallic ions and the like as well as undesired particulate matter from the tap water. The produced supply of purified water is normally passed into a temporary storage reservoir or vessel where it is ready for dispensing and use, typically by operation of an appropriate faucet valve located adjacent a kitchen sink or the like. While the specific construction and operation of the purified water supply system may vary, such systems are exemplified by the systems shown and described in U.S. Pat. Nos. 4,585,554; 4,595,497; and 4,657,674.

In many instances, it is desirable to obtain an indication of the degree of purity of the purified water supply produced by the water supply system. Alternately stated, it is desirable to obtain an indication of the operating efficiency of the semi-permeable membrane within the reverse osmosis unit. In this regard, the level of water purity will depend upon and thus will vary in accordance with several factors, such as the cleanliness of the reverse osmosis unit membrane and the degree of contamination of the incoming feed water in a raw condition. The purity level of the produced purified water is normally indicated by a measurement of electrical conductivity, wherein a relatively high electrical conductivity correlates with a relatively low resistance and reflects a substantial quantity of remaining ionic material which has not been removed by the reverse osmosis unit. Conversely, a relatively low conductivity level indicates that a high proportion of ionic material as well as other contaminants have been removed. A failure of the purified water to meet certain purification criteria as represented by conductivity level indicates that the water supply system may not be operating properly, and particularly that the semi-permeable membrane within the reverse osmosis unit may need to be cleaned or changed.

In the prior art, test devices and systems have been proposed for use in measuring the conductivity level of produced purified water in a typical purification system. In some instances, the conductivity of the purified water is compared with the conductivity level of the incoming tap water in a raw condition, wherein such comparison indicates the operational efficiency of the reverse osmosis unit. In general terms, such test devices and systems have utilized one or more electrodes for contacting the purified water and, in some cases, for contacting the incoming feed water, to obtain the desired water conductivity readings. The electrodes are coupled to an appropriate operating circuit and source of electrical power to provide the desire purity level readings which can be indicated on a master scale or by illumination of appropriate indicator lights.

In the past, water quality monitor test devices have most commonly comprised self-contained portable units for use by service personnel in testing purified water, as described, for example, in U.S. Pat. No. 3,990,066. More recently, however, water purification systems have been equipped with compact monitoring devices integrated directly into the purification system, as shown, for example, in U.S. Pat. Nos. 4,623,451, 4,806,912, 3,838,774, and 4,708,791. While such integrated test devices beneficially permit frequent and regular test readings without requiring intervention by skilled service personnel, such devices must include an appropriate power source such as a battery power supply or means for connection to a standard household electrical power circuit. In battery powered systems, however, the power consumption requirements have generally not been optimized, such that the battery power source must be replaced with undesirable frequency. Alternatively, electrical connections to the household power supply may be undesirable and/or inconvenient with respect to the mounting location of other water purification system components.

There exists, therefore, a need for an improved water quality monitor test device designed for integration directly into a water purification system, particularly wherein the improved test device operates with extremely low power consumption requirements, such that a battery power source or the like can be used with an extended operating life, and in a manner consistent with extended service of electrodes. The present invention fulfills these needs and provides further related advantages.

SUMMARY OF THE INVENTION

In accordance with the invention, an improved water quality monitor is provided for use in a water purification system, such as a purification system of the type having a reverse osmosis unit. The water quality monitor includes a control circuit in association with electrodes mounted in contact with incoming tap or feed water, and with purified water produced by the purification system. The control circuit is responsive to depression of a test button to obtain water conductivity readings for the tap and purified water, and to compare those conductivity readings to provide an indication of system performance.

In accordance with the preferred form of the invention, the control circuit is activated by a switch such as a test button adapted for manual depression to connect the circuit and the electrodes to a power supply, particularly such as a battery power source. The control circuit responds to test button depression by delivering a short duration pulse of one polarity to the electrodes. In this regard, a pair of electrodes are mounted in contact with each of the tap and purified water supplies, wherein each electrode pair is closely spaced for obtaining a water conductivity reading. The circuit includes comparator means for comparing the relative conductivities of the tap and purified water supplies in conjunction with a predetermined threshold, and for activating indicator means representing the operational state of the system, particularly such as the operating efficiency of the reverse osmosis unit in removing contaminants from the tap water. The preferred indicator means comprises a first indicator light of one color, such as green, to indicate system performance within prescribed limits, and a second indicator light of a second color, such as yellow, to indicate unacceptable system performance.

In accordance with one primary aspect of the invention, the control circuit includes means for maintaining the appropriate indicator light in an illuminated state as long as the test button is held in a depressed position, notwithstanding termination of the short duration pulse connected to the electrodes for obtaining the conductivity readings. With this arrangement, power consumption requirements of the monitor are substantially minimized and electrode service life is substantially optimized. When the test button is released, a capacitor within the control circuit discharges to provide a short duration pulse of opposite polarity to the electrodes, wherein this opposite polarity pulse protects the electrodes against corrosion and/or accumulation of ionic plating which could otherwise interfere with conductivity measurements.

Other features and advantage of the present invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENT

Figure 1:
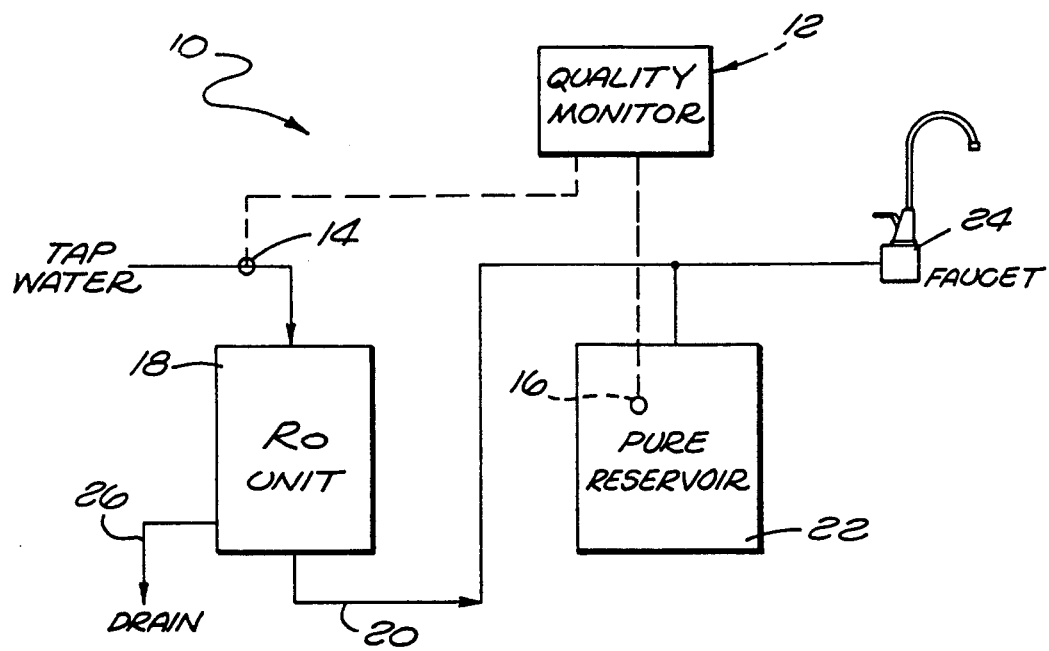
FIG. 1 is a schematic diagram illustrating a water purification system including a water quality monitor embodying the novel features of the invention.

As shown in the exemplary drawings, a water purification system referred to generally in FIG. 1 by the reference numeral 10 includes a water quality monitor 12 for monitoring and indicating the water quality level of produced purified water. The monitor 12 includes at least one electrode probe 14 mounted in a position to contact the incoming tap or feed water, and at least one additional electrode probe 16 mounted in a position to contact purified water produced by the system. These electrode probes 14 and 16 are utilized to obtain water conductivity readings which are compared and analyzed to provide an indication of water quality. In accordance with the invention, the monitor 12 is adapted for reliable and accurate water quality readings with substantially minimized power consumption requirements.

The illustrative water purification system 10 includes a reverse osmosis unit 18 for receiving and purifying an incoming supply of ordinary tap or feed water, as viewed in FIG. 1. As is known in the art, the reverse osmosis unit 18 includes an internal semi-permeable membrane (not shown) designed to separate the tap water supply into a relatively purified water supply having particulate and dissolved metallic ions removed therefrom, and a relatively impure or reject water supply having the particulate and dissolved ions concentrated therein. In normal system operation, the purified supply is coupled through a conduit 20 for storage within a suitable reservoir 22 ready for dispensing and use upon opening of a faucet valve 24 or the like. The reject water supply, sometimes referred to as brine, is normally discharged through an appropriate conduit 26 to a suitable waste or drain.

Figure 2:
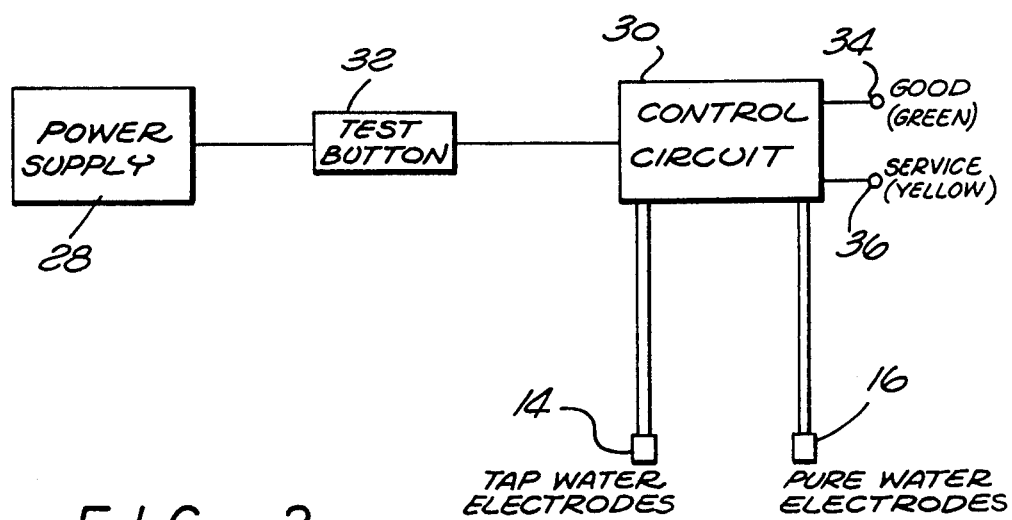
FIG. 2 is a schematic diagram illustrating operational components of the water quality monitor.

The water quality monitor 12 of the present invention is integrated into the water purification system 10 in a manner permitting a water quality test to be conducted quickly and easily, and at virtually any time, without interrupting normal operation of the purification system. As viewed in FIG. 2, the monitor 12 includes a suitable power supply 28, particularly such as a 9 volt battery or the like for operating a control circuit 30 upon manual depression of a test button 32. As will be described in more detail, the control circuit 30 is designed for brief, momentary connection of electrical power to the electrode probes 14 and 16 for purposes of obtaining comparative conductivity readings of the tap and purified water supplies. In this regard, it is known that the electrical conductivity of the water provides an indication of the quantity of dissolved and suspended contaminants, such that a relatively high conductivity reading represents a relatively high contamination level. The control circuit 30 obtains the comparative conductivity reading of the tap water to the purified water, and then compares this conductivity reading with a selected threshold level to determine the operational state of the water purification system. When the operation of the system 10 is within satisfactory limits, as represented by a substantial proportional reduction in electrical conductivity in the purified water relative to the tap water, which indicates substantial proportional removal of dissolved ions, the control circuit 30 illuminates a first indicator light 34. Alternatively, when operation of the system 10 is unsatisfactory, as evidenced by a comparatively high conductivity reading for the purified water, a second indicator light 36 is illuminated. In the preferred form, the indicator lights 34 and 36 are respectively colored green and yellow, and thus correlate with standard colors respectively representative of acceptable and unacceptable conditions. When the yellow light 36 is illuminated, appropriate remedial action can be taken to correct system operation, wherein such remedial action typically involves cleaning or replacement of the semi-permeable membrane within the reverse osmosis unit 18.

Figure 3:
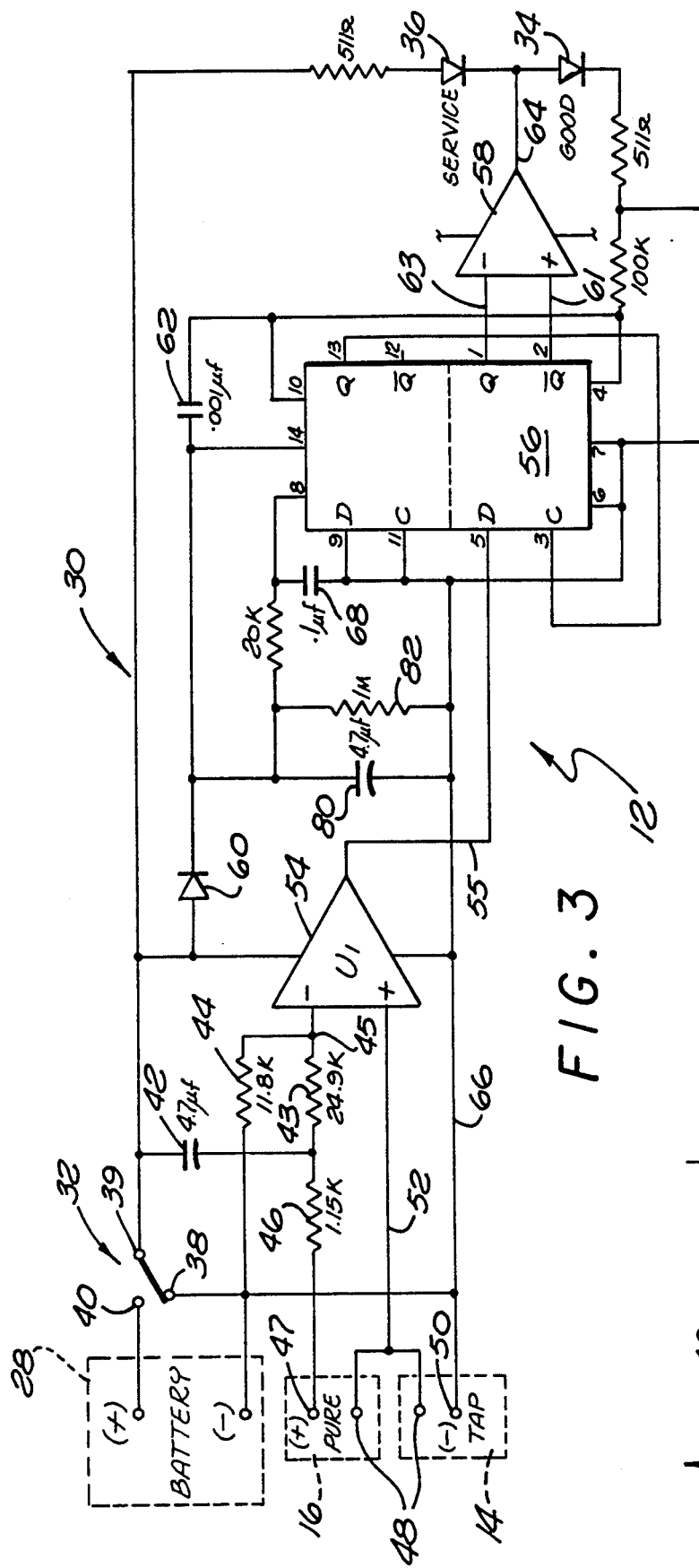
FIG. 3 is an electrical circuit diagram, shown somewhat in schematic form, depicting one preferred control circuit for use with the invention.

A preferred circuit configuration for the control circuit 30 is shown in FIG. 3. More specifically, the test button 32 comprises a manually depressible spring-loaded button which is normally biased by a spring (not shown) toward a position bridging contacts 38 and 39. In this position, the button 32 is spaced from a battery contact 40 to disconnect a positive terminal of the power source 28 from the circuit.

Manual depression of the test button 32 bridges the contacts 39 and 40 to initiate charging of a primary capacitor 42. The capacitor 42 is coupled between the battery terminals within a circuit which includes parallel circuit paths used to obtain a comparative conductivity reading for the purified and tap water supplies in relation to a performance threshold representing acceptable operational efficiency of the purification system. More specifically, one of these paths includes series connected resistors 43 and 44, wherein these resistors have selected values for in-series voltage drops such that an intermediate junction 45 comprises a selected proportional voltage. The second path includes a resistor 46 and the electrode probes 14 and 16 in series. In this regard, the purified water probe 16 comprises a primary electrode 47 in spaced relation with a secondary electrode 48 linked electrically to a common secondary electrode 48 of the tap water probe 14. This secondary electrode 48 of the tap water probe 14 is also mounted in spaced relation with a primary probe 50 connected to the negative battery terminal.

Figure 4:
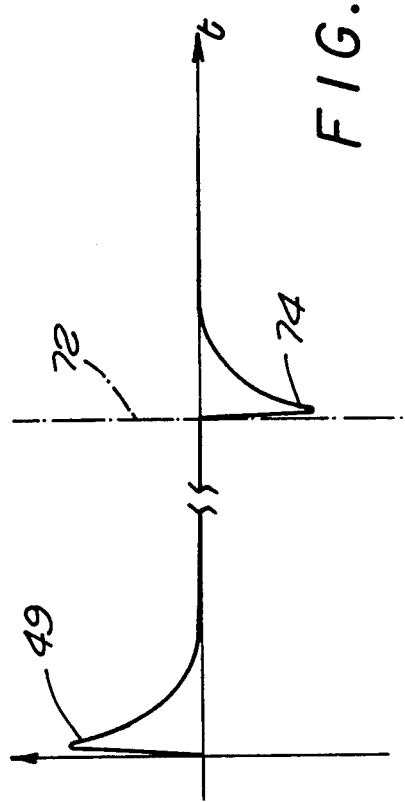
FIG. 4 is a graphic representation of opposite polarity pulses generated by the control circuit of FIG. 3.

Charging of the primary capacitor 42 is thus effective to couple a short duration pulse 49 of positive voltage as viewed in FIG. 4. This short pulse 49 momentarily continues until the capacitor 42 is charged. During charging, a voltage is applied across the electrodes of the two probes 14 and 16, with the voltage at the common secondary electrodes 48 providing a comparative indication of the conductivities of the purified and tap water supplies. By comparing the voltage at the secondary electrodes 48 with the selected threshold voltage at junction 45 between the resistors 43 and 44, the control circuit 30 indicates whether the performance efficiency of the system 10 is above or below the selected threshold. In this regard, the resistor values depicted in FIG. 3 define an acceptable threshold when the conductivity of the purified water is reduced by at least seventy percent in comparison with the incoming tap water, although it will be understood that other resistor values may be used for selecting other threshold performance points. Importantly, the pulse 49 used to determine conductivity is very brief in time to minimize overall circuit power requirements.

A conductor 52 connected to the common electrodes 48 is connected to a positive terminal of an operational amplifier 54. The negative terminal of the op-amp 54 is linked to the intermediate junction 45 between the resistors 43 and 44. With this arrangement, the op-amp 54 provides a comparison means for comparing the relative voltage drops through the purified and tap water supplies, which represents the comparative conductivities of the water supplies with the threshold point voltage drop between the resistors 43 and 44. Whenever the voltage at the positive electrode on conductor 52 exceeds the voltage at the negative electrode at junction 45, the circuit indicates that the voltage drop represented by purified water conductivity is insufficient in relation to the target voltage drop at the negative electrode. Such insufficient voltage drop represents unacceptable performance of the purification system, and triggers the op-amp 54 to provide a positive output of about 9 volts on an output line 55. Alternatively, if the voltage at the positive terminal of the op-amp 54 is less than the voltage at the negative terminal, such comparison represents acceptable operation of the purification system, and results in a substantially zero voltage output on the conductor 55.

The output conductor 55 is connected to a dual stage flip-flop 56, such as a CMOS 4013. In general terms, depending upon the output on the conductor 55, the flip-flop 56 signals a secondary amplifier 58 to illuminate one of the two indicator lights 34 and 36, as represented by LEDs in the circuit diagram.

More particularly, when the test button 32 is depressed, the positive terminal of the power supply 28 is also connected through a diode 60 to charge a reset capacitor 62. This reset capacitor 62 has a relatively low capacitance, in comparison with the primary capacitor 42, and thus charges substantially instantaneously to provide a positive voltage to the reset pins labeled 4 and 10 of the dual stage flip-flop 56. Positive voltages at these pins serve to reset the dual stages, resulting in low or substantially zero voltage outputs at the "Q" pins 13 and 1, while providing comparatively high outputs in digital form at the "not Q" output pins 12 and 2. Accordingly, the output pins 1 and 2 of the second flip-flop stage connect a high output on conductor 61 to the positive terminal of the secondary amplifier 58, and a low output on conductor 63 to the negative terminal, resulting in a high output provided on the conductor 64 to a junction between the LEDs 34 and 36. This high output connects positive voltage across the "good" LED 34, resulting in illumination thereof, with the LED 34 being connected through the conductor 66 to the negative battery terminal.

A set capacitor 68 is also charged through the diode 60 when the test button 32 is depressed. The relative capacitance of the set capacitor 68 is chosen to charge at a slower rate than the reset capacitor 62, but at a rate significantly faster than the primary capacitor 42. A preferred charge interval on the order of a few milliseconds, obtained by use of the capacitance values depicted in FIG. 3, applies a positive voltage to flip-flop set pin 8 which switches the output state of the pins 12 and 13 on the first stage. The now-high output at pin 13 is coupled to a clock pin 3 on the second stage causing the second flip-flop stage to latch and store the incoming data on the conductor 55 at pin 5.

When the signal at flip-flop pin 5 is low, representing acceptable performance of the purification system, the outputs at the pins 1 and 2 remain unchanged and the LED 34 remains illuminated. However, when the signal at pin 5 is high, representing unacceptable performance, the outputs at pins 1 and 2 are reversed to result in a low voltage on conductor 64. The presence of a low or substantially zero voltage on the conductor 64 results in a positive signal across the second LED 36 for illumination thereof. Accordingly, when system performance is unacceptable, the "good" LED 34 initially illuminates as a brief blink for the charge time of the set capacitor 68 and then de-energizes as the "service" LED 36 is illuminated in response to a low signal on the conductor 64. Importantly, regardless of the circuit state, the flip-flop 56 maintains illumination of the appropriate LED for the duration of depression of the test button 32, irrespective of the brief duration of the pulse 49 used to obtain the conductivity readings.

When the test button 32 is released, as represented by the time line 72 in FIG. 4, the amplifiers 54 and 58 are immediately disconnected from the power supply 28 and the illuminated indicator light 34 or 36 is promptly extinguished. However, upon release, the test button 32 is switched to a position bridging the contacts 38 and 39, thereby discharging the primary capacitor 42 in a reverse direction across the electrode probes 14 and 16. The capacitor 42 thus discharges through the probes with a short duration current pulse 74 of negative voltage, wherein this opposite polarity pulse is highly effective in reducing or eliminating corrosion of the metallic probes and/or ionic plating and related coating which can otherwise interfere with accurate conductivity readings.

A delay capacitor 80 is also provided in the control circuit to prevent repetitive conductivity readings at extremely short intervals. In this regard, such repetitive readings can result in unacceptable ionization of water in the region of the probes 14 and 16, with a corresponding distortion in conductivity readings. The delay capacitor 80 maintains the flip-flop 56 in a latched condition for a minimum time period following a test reading, to permit ionic equilibration in and about the probes.

More specifically, while the test button 32 is depressed, the delay capacitor 80 charges. When the test button 32 is released, the capacitor 80 is discharged over a period of several seconds through a resistor 82, wherein this slow discharge maintains a positive voltage at the terminal 14 of the flip-flop 56 for a period of several seconds. This maintenance of a positive voltage at the pin 14 prevents reset of the flip-flop in response to charging of the reset capacitor 62, as previously described.

The improved water quality monitor of the present invention thus provides minimal power consumption and extends electrode life by supplying a short duration pulse of one polarity to electrode probes for use in obtaining comparative conductivity readings. The resultant readings provide an appropriate output to indicator lights which remain illuminated in a latched condition for the duration of test button depression. When the test button is released, the illuminated indicator light is extinquished and an opposite polarity pulse of short duration is discharged across the electrode probe to prevent plating and corrosion.

A variety of modifications and improvements to the present invention will be apparent to those skilled in the art. Accordingly, no limitation on the invention is intended by way of the foregoing description and accompanying drawings, except as set forth in the appending claims.

What is claimed is:

1. A water quality monitor for use in a water purification system or the like adapted to produce a relatively purified water supply from a tap water supply, said water quality monitor comprising:
   electrode means for contacting a tap water supply and a relatively purified water supply produced from the tap water supply by a purification system;
   circuit means having a switch movable manually between first and second positions and including means activated upon movement of said switch to said first position for generating a short duration pulse of one polarity and for delivering said pulse to said electrode means, said circuit means further including means for determining ratios of the conductivities of the tap and purified water supplies and for comparing said ratios with a selected threshold representing satisfactory operating performance of the purification system and for generating the of first and second outputs respectively representing satisfactory and unsatisfactory system performance; and
   indicator means responsive to said one of said first and second outputs to indicate system performance;
   said circuit means further including means for maintaining said indicator means in an operation state to indicate system performance while said switch is in said first position, and for a duration, independent of, and potentially longer than the duration of said pulse of one polarity, said circuit means further including means for generating and deliverying a short duration pulse of opposite polarity to said electrode means upon movement of said switch to said second position.

2. The water quality monitor of claim 1 wherein said indicator means comprises a pair of indicator lights.

3. The water quality monitor of claim 1 wherein said indicator means comprises a pair of indicator lights of different colors.

4. The water quality monitor of claim 1 wherein said electrode means comprises first and second electrode pairs respectively contacting the tap water supply and the purified water supply.

5. The water quality monitor of claim 4 wherein said first and second electrode pairs are connected in series.

6. The water quality monitor of claim 1 wherein said circuit means further includes reset means for resetting said circuit means upon movement of said switch to said first position.

7. The water quality monitor of claim 6 wherein said circuit means further includes time delay means for disabling said reset means for a predetermined minimum time delay period following movement of said switch to said second position.

8. The water quality monitor of claim 1 wherein said switch comprises a spring-loaded switch biased normally toward said second position.

9. A water quality monitor for use in a water purification system or like adapted to produce a relatively purified water supply from a tap water supply, said water quality monitor comprising:
   electrode means for contacting a purified water supply produced from a tap water supply by a purification system;
   circuit means having a switch movable manually between first and second positions and including means activated upon movement of said switch to said first position for generating a short duration pulse and for deliverying said pulse to said electrode means, said circuit means further including means for determining the conductivity of the purified water supply in comparison with a selected threshold representing satisfactory operating performance of the purification system and for generating one of first and second outputs respectively representing satisfactory and unsatisfactory system performance; and
   indicator means responsive to said one of said first and second outputs to indicate system performance;
   said circuit means further including means for maintaining said indicator means is an operative state to indicate system performance while said switch is in said first position, and for a duration, independent of, and potentially longer than, the duration of said pulse.

10. The water quality monitor of claim 9 wherein said indicator means comprises a pair of indicator lights of different colors.

11. The water quality monitor of claim 9 wherein said short duration pulse has a first polarity, said circuit means further including means for generating and connecting a short duration pulse of a second, opposite polarity to said electrode means upon movement of said switch to said second position.

12. The water quality monitor of claim 9 wherein said switch comprises a spring-loaded switch biased normally toward said second position.

13. A water quality monitor for use in a water purification system or the like adapted to produce relatively purified water supply from a tap water supply, said water quality monitor comprising:
- a first electrode probe contacting a tap water supply, said first probe including a pair of electrodes in predetermined spaced relation;
- a second electrode probe contacting a relatively purified water supply produced from the tap water supply by a purification system, said second probe including a pair of electrodes in predetermined spaced relation;
- test switch means movable manually between first and second positions;
- circuit means responsive to movement of said test switch means to said first position to generate a short duration pulse of one polarity and to deliver said pulse in series to said first and second probes;
- said circuit means further including comparator means for comparing the voltage at a junction between said first and second probes with a selected threshold voltage representative of acceptable operating performance of the purification system, and for generating one of first and second outputs in response thereto wherein said first and second outputs respectively represent satisfactory and unsatisfactory system performance; and
- first and second indicator means, said circuit means further including latch means responsive to said one of said first and second outputs for activating said first indicator means when system performance is satisfactory and for activating said second indicator means when system performance is unsatisfactory, said latch means maintaining the appropriate one of the first and second indicator means is an activated state to indicate system performance while said switch means is in said first position, for a duration, independent of potentially longer than, the duration of said pulse of one polarity, said circuit means further including means for generating and deliverying a short duration pulse of opposite polarity to said first and second probes upon movement of said switch means to said second position.

14. The water quality monitor of claim 13 wherein said test switch means comprises a spring-loaded switch biased normally toward said second position.

15. A water quality monitor for use in a water purification system or the like adapted to produce a relatively purified water supply from a tap water supply, said water quality monitor comprising:
- electrode means for contacting a relatively purified water supply produced from a tap water supply;
- circuit means connected to said electrode means and including test switch means movable manually between first and second positions, said circuit means including means for delivering a short duration pulse to said electrode means up movement of said test switch means to said first position, and for generating an output signal representative of conductivity of the purified water supply; and
- indicator means responsive to said output signal to indicate the conductivity of the purified water supply, said circuit means including means for maintaining said indicator means in a state indicating said conductivity for a duration, independent of, and potentially longer than, the duration of said pulse until said test switch means is moved from said first position to said second position.

16. The water quality monitor of claim 15 wherein said short duration pulse has a first polarity, said circuit means further including means for generating and connecting a short duration pulse of a second, opposite polarity to said electrode means upon movement of said switch to said second position.

17. The water quality monitor of claim 15 wherein said test switch means comprises a spring-loaded switch biased normally toward said second position.

* * * * *